US010292878B2

(12) United States Patent
Perez

(10) Patent No.: US 10,292,878 B2
(45) Date of Patent: May 21, 2019

(54) SYSTEM FOR FIXATION OF FLEXIBLE STRETCHER TO HARD STRETCHER

(71) Applicant: Ricardo Perez, Votorantim (BR)

(72) Inventor: Ricardo Perez, Votorantim (BR)

( * ) Notice: Subject to any disclaimer, the term of this patent is extended or adjusted under 35 U.S.C. 154(b) by 31 days.

(21) Appl. No.: 15/724,886

(22) Filed: Oct. 4, 2017

(65) Prior Publication Data

US 2018/0092789 A1 Apr. 5, 2018

(30) Foreign Application Priority Data

Oct. 4, 2016 (BR) ............................ 202016023173

(51) Int. Cl.
*A61G 1/013* (2006.01)
*A61G 1/044* (2006.01)
*A61G 7/10* (2006.01)
*A61F 5/37* (2006.01)
*A61G 1/00* (2006.01)

(52) U.S. Cl.
CPC ............... *A61G 1/044* (2013.01); *A61G 1/00* (2013.01); *A61G 1/013* (2013.01); *A61G 7/10* (2013.01)

(58) Field of Classification Search
CPC .......... A61G 1/044; A61G 1/013; A61G 1/00; A61G 1/10; A61G 7/1023
See application file for complete search history.

(56) References Cited

U.S. PATENT DOCUMENTS 2,489,828 A * 11/1949 Springer .................. A61G 1/01 5/625
5,839,137 A * 11/1998 Butler ...................... A61G 1/01 5/627
6,135,115 A * 10/2000 Rodarte ................ A61F 5/3776 128/869
6,363,936 B1 * 4/2002 McCormick ........... A61G 1/044 128/870
7,168,110 B2 * 1/2007 Girard ...................... A61G 1/01 5/627
7,222,378 B2 * 5/2007 DuPree .................... A61G 1/01 5/625
2002/0162171 A1 * 11/2002 Faz ........................ A61G 1/013 5/627

(Continued)

FOREIGN PATENT DOCUMENTS

| | | |
|---|---|---|
| CA | 2 454 139 | 6/2005 |
| GB | 2 487 464 | 7/2012 |
| WO | WO-91/03221 | 3/1991 |

OTHER PUBLICATIONS

European Search Report dated Jan. 24, 2018 in corresponding European Application No. 17 19 4689.

*Primary Examiner* — Eric J Kurilla
*Assistant Examiner* — Rahib T Zaman
(74) *Attorney, Agent, or Firm* — B. Aaron Schulman, Esq.; Stites & Harbison, PLLC

(57) ABSTRACT

This present invention describes a system for fixation of a flexible stretcher to a hard stretcher, comprising multiple belts made of flexible material affixed via a multiplicity of strap adjusters and bars to the flexible stretcher, and a flexible and adjustable cross connection belt, which, because of their disposition and technical characteristics, enable fixation of the hard stretcher, together with a victim individual, to the body of the flexible stretcher, making the movement of the individual from one stretcher to another unnecessary.

2 Claims, 5 Drawing Sheets

(56) References Cited

U.S. PATENT DOCUMENTS

| | | | | |
|---|---|---|---|---|
| 2004/0088794 | A1 * | 5/2004 | Calkin | A61G 1/01 5/628 |
| 2006/0289573 | A1 * | 12/2006 | Mantuano, Jr. | A61G 1/00 224/157 |
| 2009/0313759 | A1 * | 12/2009 | Wong | A61G 1/01 5/627 |
| 2012/0272451 | A1 * | 11/2012 | Haskell | A61G 1/01 5/628 |
| 2015/0082544 | A1 * | 3/2015 | Yancovitch | A61G 1/017 5/628 |

* cited by examiner

SYSTEM FOR FIXATION OF FLEXIBLE STRETCHER TO HARD STRETCHER

FIELD OF THE INVENTION

The present invention relates generally to stretchers for transporting individuals under a variety of circumstances, and in particular to a system having safety belts that may be applied to a flexible stretcher for fixation to a hard stretcher.

BACKGROUND OF THE INVENTION

Of the currently existing rescue stretchers currently on the market, all are built for independent and specific use at the time of rescue. An example is hard rescue stretchers, where a victim is moved onto the hard stretcher until they are transferred to another stretcher, or flexible rescue stretchers, which are built for rescue in places that are difficult to access, and for difficult maneuvers such as vertical rescue operations. The victim and/or individual is always carried upon either a hard or a flexible stretcher, and must be transferred and moved from one type of stretcher to the other if and when needed. The system of the present invention as applied to flexible stretchers for fixing to hard stretchers is innovative, as it makes movement of an individual from one type of stretcher to another unnecessary, by affixing the hard stretcher to a flexible stretcher.

Currently existing flexible stretchers fulfill only one function attributed to them, without extensions or other facilities aggregated to them. Hard stretchers are used almost exclusively in land operations, while flexible stretchers are used for places of difficult access and for vertical rescue operations. When the rescue of an individual is performed first using a hard stretcher, if there is a need to move the individual to a more flexible stretcher, due to, for example, difficulties extracting the individual, the individual is transferred from one type of stretcher or equipment to the other, increasing their risk of injury, as well as impairing the agility and endangering the safety of the persons facilitating the rescue.

As described above, there remains a lack of efficient solutions for the transport of victims and/or individuals within a complex field setting, due to the differences in parts between the various types of equipment used, as well as the requirements for transfer and/or movement of individuals when there is a need to transition between various types of rescue means. What is needed therefore, is a system that allows for an easy transition between hard and flexible stretchers, such as is described in the present invention, to enable the optimizing of handling of individuals in emergency situations, especially in situations where the handling is done outside of a hospital or controlled setting, by people such as paramedics.

SUMMARY OF THE INVENTION

The present application seeks to provide a system for facilitating the rescue of individuals in places that are extraordinarily difficult to access, for example very high places, by making the transfer of an individual from one piece of equipment to another unnecessary. This reduces the time required for a rescue operation, thereby making it safer and more efficient. With the individual immobilized on a hard stretcher, the present invention allows the hard stretcher to be affixed to a flexible stretcher via a system having multiple flexible belts fixed with resilient strap adjustors and bars applied on the flexible stretcher. This system enables the removal of an individual from places of difficult access and/or those requiring vertical movements, and allows the optimization of handling of persons in emergency situations, especially where the individual and/or victim is being attended by emergency personal such as paramedics in an extra-hospital setting.

DETAILED DESCRIPTION OF THE INVENTION

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

Figure 1:
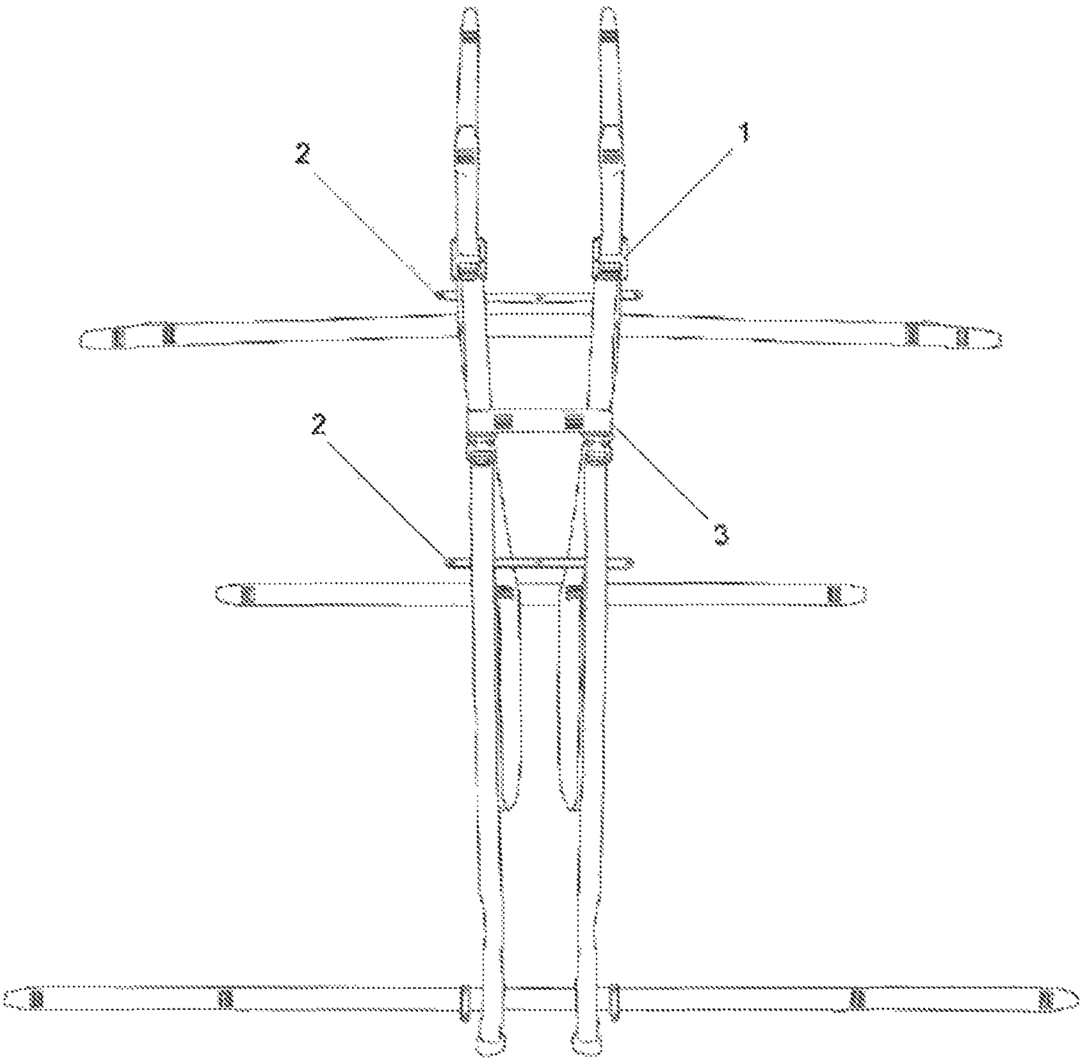
FIG. 1 is a top view of the set of flexible safety belts.
Figure 2:
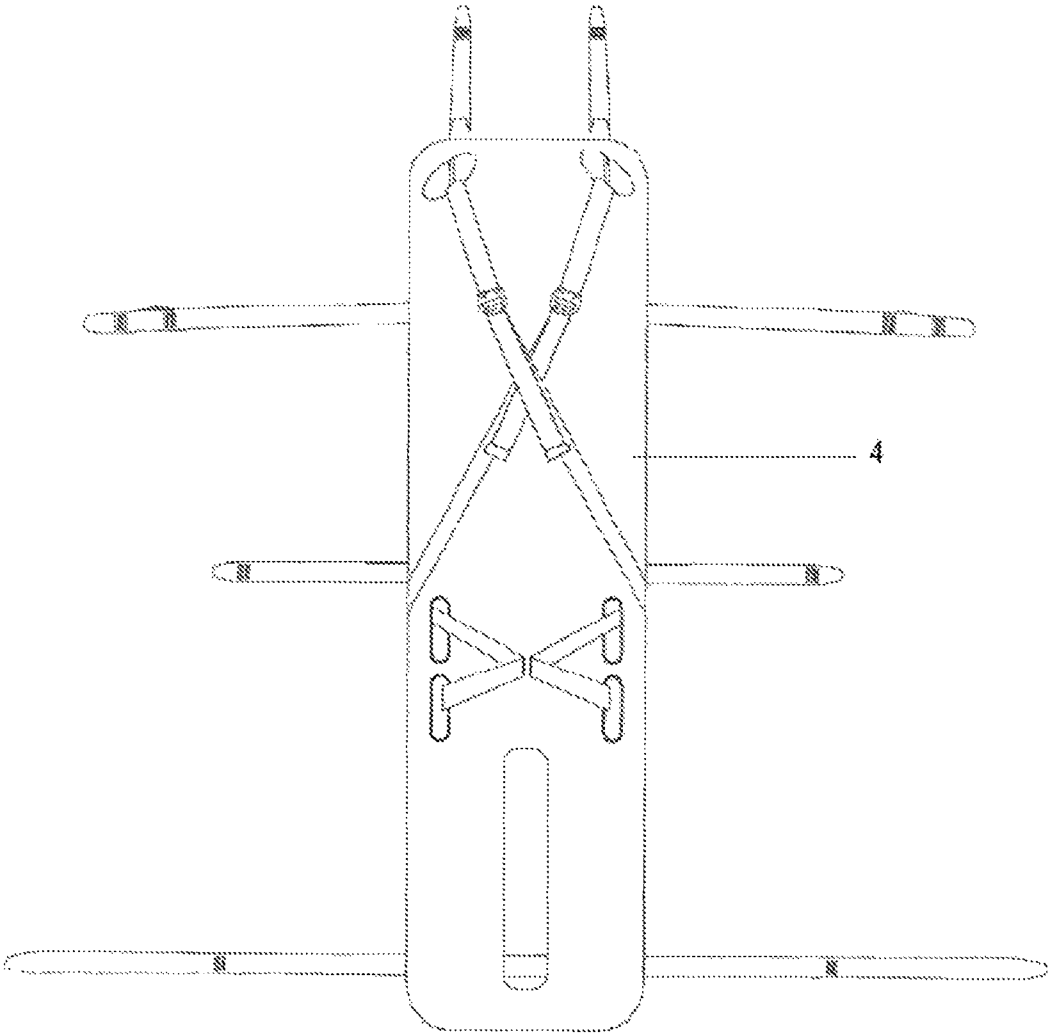
FIG. 2 is a top view of a hard stretcher fixed to the set of safety belts of the flexible stretcher.
Figure 3:
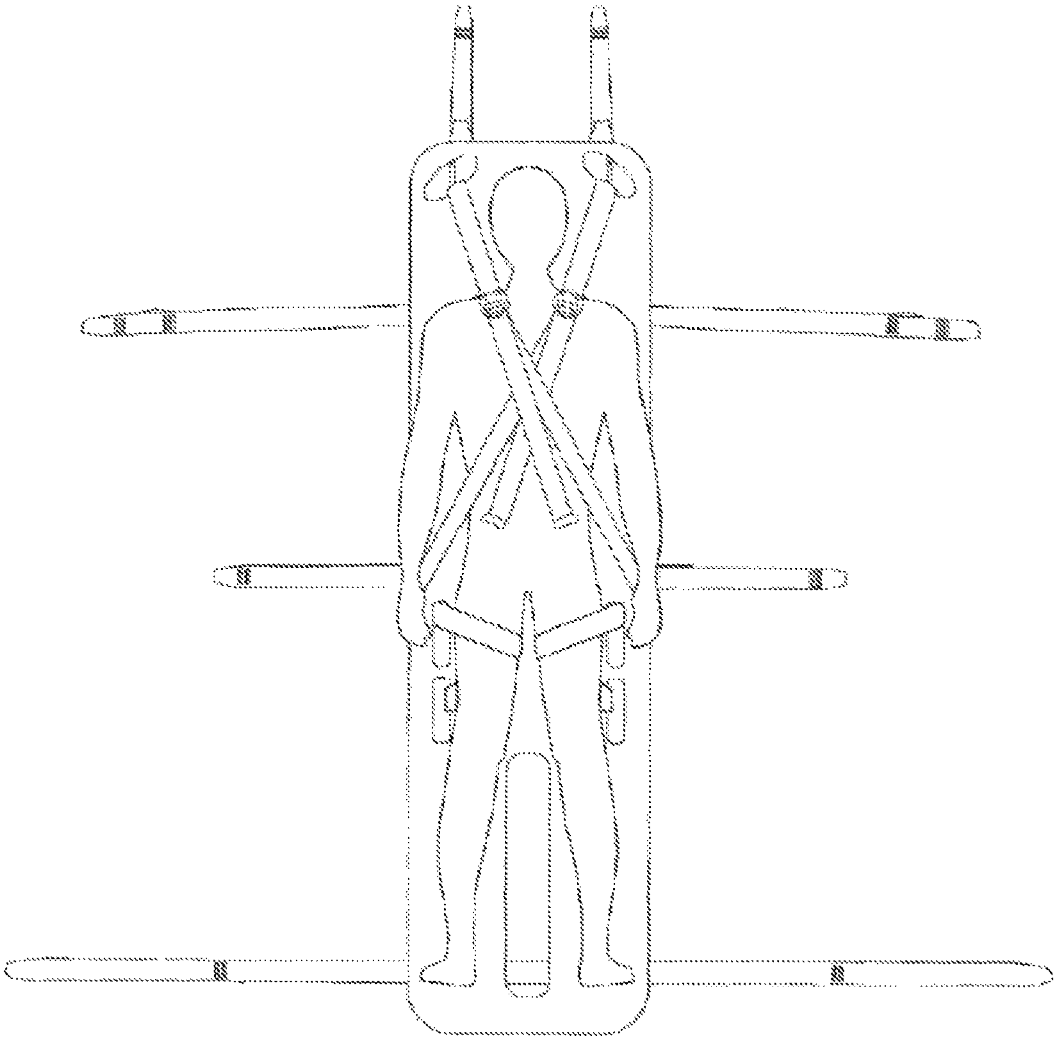
FIG. 3 is a top view of an individual fixed to the hard stretcher and the set of safety belts of the flexible stretcher.
Figure 4:
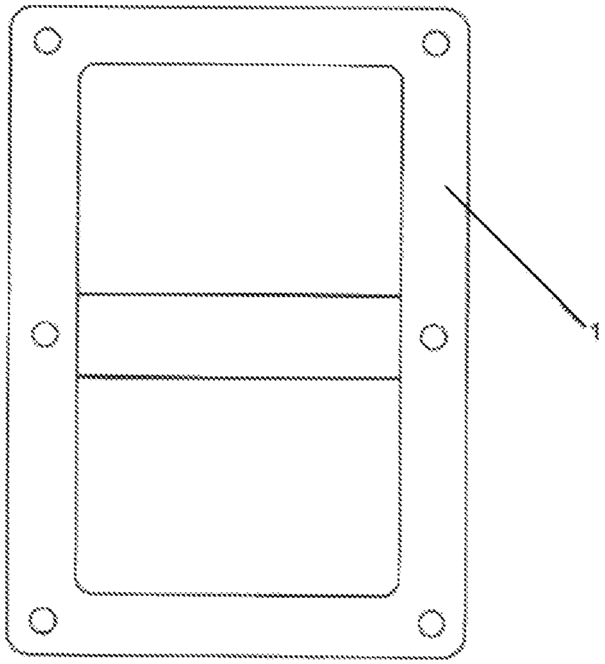
FIG. 4 is a top view of an upper strap adjustor.
Figure 5:
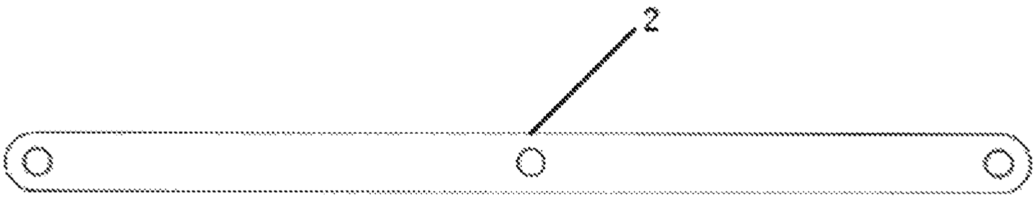
FIG. 5 is a view of a lower bar.
Figure 6:
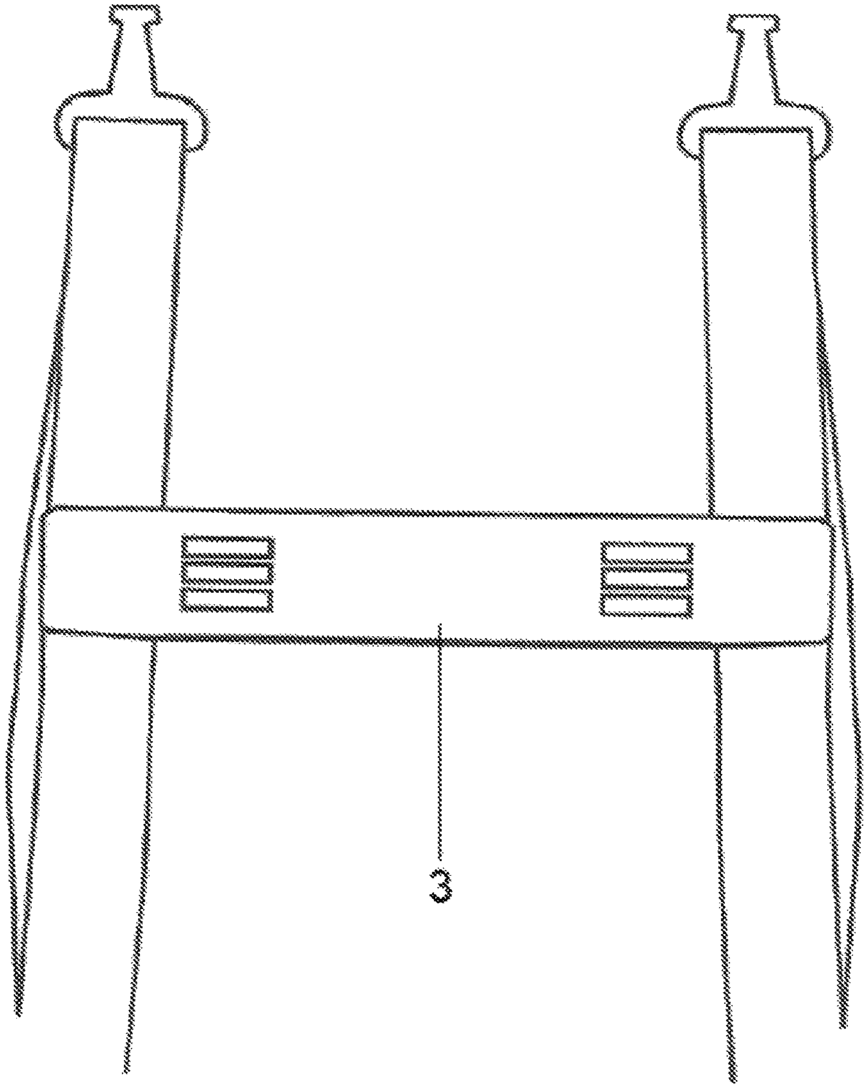
FIG. 6 is a partial zoomed view of FIG. 1, illustrating the adjustable cross connection belt.

The present invention includes a system of flexible belts applied to a flexible stretcher for fixation of the flexible stretcher to a hard stretcher (4). FIG. 1 shows a top view of the set of flexible safety belts, which comprises a multiplicity of flexible safety belts sewn together, and affixed to the flexible stretcher through a set of upper strap adjustors (1) and lower (2) bars, both being made of a resilient material, the set also comprising one flexible cross-connection belt (3) of adjustable height, fixed by seams and hook-and-loop fasteners such as Velcro®. The set enables fixing a hard stretcher, as illustrated in FIG. 2, together with the rescued individual, as illustrated in FIG. 3, to the flexible stretcher. The resilient material can be a metal, such as stainless steel or titanium, or another resilient material, such as carbon fibre. The embodiment illustrated in the Figures includes a pair of upper parallel belts running along and beyond the length of the individual, and three parallel lower belts positioned perpendicularly to the upper belts, and running across the width of the individual, with the flexible cross-connection belt also positioned perpendicularly to the upper belts.

The flexible cross connection belt (3) has been included in the set of flexible safety belts, because it enables fixation of an individual directly to the flexible stretcher, by joining the upper parallel belts, and simultaneously promoting the individual's comfort and safety. The cross-connection belt prevents the separation of the parallel belts when an individual is fixed to the flexible stretcher. The flexible cross connection belt become unnecessary if and when the individual is fixed to a hard stretcher (4), at which point the flexible cross-connection belt is adjusted in height and moved behind the hard stretcher, enabling the crossing of the parallel belts for fixation of the hard stretcher holding the individual, to the flexible stretcher.

The upper strap adjustors (1) are fixed to the flexible stretcher via multiple holes, having their central portions left free and open for the through passage of the parallel belts, thus enabling the adjustment of the length of the parallel belts according to the hard stretcher and individual's size.

The lower bars (2) are also fixed to the flexible stretcher via multiple holes, where the portions of the lower bars that are not connected to the stretcher form intermediary voids between the bars and the flexible stretcher, the voids being free for the passage of the parallel belts, thereby enabling adjustment of the length of the parallel belts according to the size of the hard stretcher and the individual.

The invention claimed is:

1. A system for fixation of a flexible stretcher to a hard stretcher, the system comprising: a flexible stretcher; and a set of multiple flexible safety belts sewn together and affixed to the flexible stretcher, the set having upper parallel belts positioned running parallel along the height of an individual, and lower parallel belts positioned perpendicularly to the upper belts, running across the width of the individual, the flexible safety belts also comprising: a multiplicity of upper strap adjustors fixed to the flexible stretcher and positioned on an upper portion of the upper parallel belts, having open interior regions allowing passage of the upper parallel belts individually through a central portion of the strap adjustors; a multiplicity of lower bars fixed to the flexible stretcher via multiple holes, wherein central portions of the bars that are not fixed to the flexible stretcher form intermediary voids between the bars and the flexible stretcher, the voids allowing passage of the parallel belts between the bars and the flexible stretcher, enabling adjustment of the length of the upper parallel belts according to the size of a hard stretcher and the individual; and an adjustable flexible cross-connection belt, positioned perpendicularly to and joining the parallel upper belts and fixed via seams and hook-and-loop fasteners, allowing adjustment of the height of the cross-connection belt, and impeding separation of the parallel belts, wherein the cross-connection belt allows fixation of the individual directly to the flexible stretcher, and the cross-connection belt is adjusted in height and moved behind the hard stretcher during fixation of the hard stretcher to the flexible stretcher, allowing crossing of the parallel belts for fixation of the hard stretcher holding the individual to the flexible stretcher.

2. The system of claim 1, wherein the upper strap adjustors and the lower bars are of a material selected from the group consisting of: stainless steel, titanium, and carbon fiber.

* * * * *